(12) United States Patent
Reutemann et al.

(10) Patent No.: US 7,309,403 B2
(45) Date of Patent: Dec. 18, 2007

(54) METHOD FOR AVOIDING CORROSION

(75) Inventors: Werner Reutemann, Bobenheim-Roxheim (DE); Theodor Weber, Ludwigshafen (DE); Karl-Heinz Ross, Grünstadt (DE); Manfred Julius, Limburgerhof (DE)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 10/572,783

(22) PCT Filed: Sep. 24, 2004

(86) PCT No.: PCT/EP2004/010766

§ 371 (c)(1),
(2), (4) Date: Jun. 8, 2006

(87) PCT Pub. No.: WO2005/030697

PCT Pub. Date: Apr. 7, 2005

(65) Prior Publication Data

US 2006/0243584 A1    Nov. 2, 2006

(30) Foreign Application Priority Data

Sep. 24, 2003   (DE) ................. 103 44 282

(51) Int. Cl.
*B01D 3/38* (2006.01)
*B01D 3/40* (2006.01)
*C07C 209/86* (2006.01)
*C07C 209/90* (2006.01)

(52) U.S. Cl. ............... 203/7; 203/37; 203/18; 203/78; 203/79; 203/99; 203/DIG. 19; 203/DIG. 23; 564/499; 568/916

(58) Field of Classification Search ............. 203/7.37, 203/79, 78, 99, DIG. 19, 18, DIG. 23, 100; 564/499, 493, 497; 568/916, 920
See application file for complete search history.

(56) References Cited

U.S. PATENT DOCUMENTS 3,120,525 A * 2/1964 Muhlbauer et al. ......... 544/352

(Continued)

FOREIGN PATENT DOCUMENTS

EP    0 037 695    10/1981

(Continued)

OTHER PUBLICATIONS

Chemical Abstracts, Bd. 55, Nr. 24 (1961), Abstract No. 2444891, A. M. Sukhotin et al.: o "Corrosion of Installations for the Production of Methylamines".

*Primary Examiner*—Virginia Manoharan
(74) *Attorney, Agent, or Firm*—Connolly Bove Lodge & Hutz

(57) ABSTRACT

The invention relates to a method of avoiding corrosion in the separation of methylamine from a product stream (10) which is obtained in the preparation of methylamines by gas-phase reaction of methanol and ammonia and includes monomethylamine, dimethylamine, trimethylamine, ammonia and methanol as components, where ammonia is separated off by pure distillation in a first column (1), the remaining components of the product stream obtained as bottoms (12) are fed to a second column (2). Trimethylamine (14) is separated off in the second column (2) by extractive distillation with introduction of water. The further of the product stream obtained as bottoms (15) from the second column (2) are fed to a third column (3), in which monomethylamine and dimethylamine are separated off at the top. The monomethylamine and dimethylamine are separated by distillation in a fourth column (4). To avoid corrosion alkali metal hydroxide is added to the second or third column (3).

8 Claims, 1 Drawing Sheet

U.S. PATENT DOCUMENTS 3,850,760 A * 11/1974 Lenel et al. .................. 203/84
4,283,254 A *  8/1981 Binau et al. .................. 203/4
6,986,833 B2     1/2006 Wölfert et al.

FOREIGN PATENT DOCUMENTS

EP    1 312 599    5/2003
JP   67-108041     7/1982

* cited by examiner

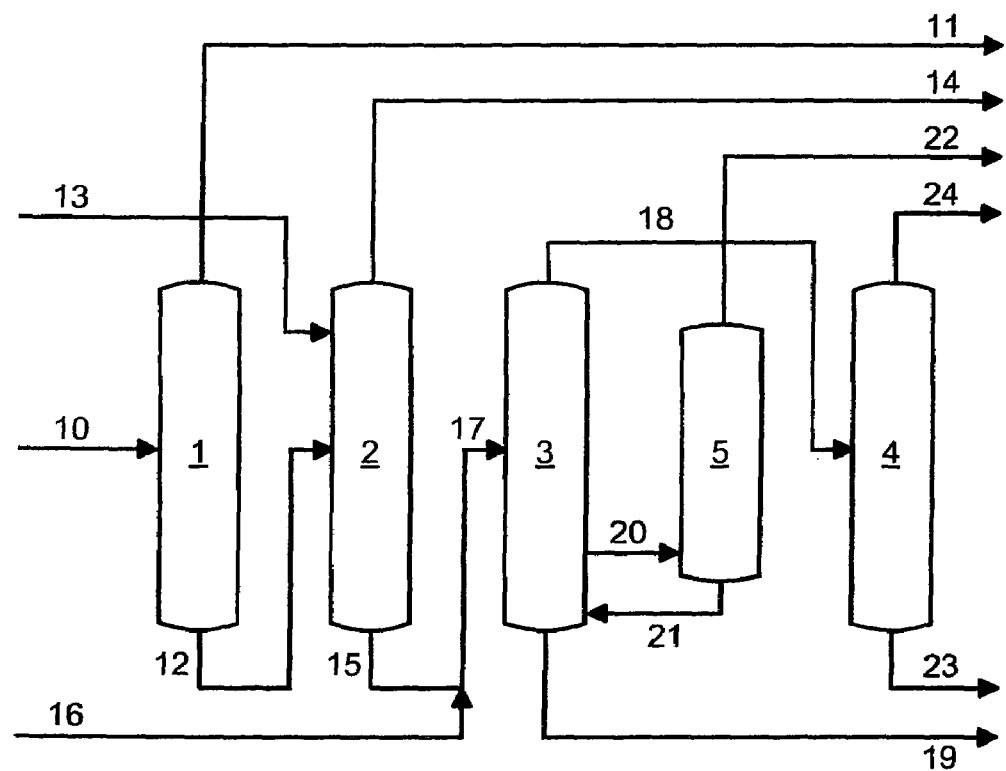

METHOD FOR AVOIDING CORROSION

RELATED APPLICATIONS

This application is a national stage application (under 35 U.S.C. 371) of PCT/EP2004/010766 filed Sep. 24, 2004 which claims benefit to German application 103 44 282.0 filed Sep. 24, 2003.

The present invention relates to a method of avoiding corrosion in the separation of methylamines from a product stream obtained in the preparation of methylamines.

The reaction of methanol and ammonia in the presence of a heterogeneous catalyst based on aluminum oxide forms monomethylamine, dimethylamine and trimethylamine. The reaction to form the methylamines is exothermic and occurs at from 390 to 430° C. Since the reactions to form methylamines are equilibrium reactions, not only methylamines but also ammonia and methanol are present in the product stream.

After the reaction, the product gas stream is passed to a distillation plant. In the distillation plant, the product gas stream is separated into the individual components. In the distillation plants used at present, ammonia is separated off in a first column forming an azeotrope with trimethylamine, whereby also a part of the trimethylamine is distilled off, trimethylamine is separated off in a second column and water, which generally contains methanol which has not been reacted in the reaction, is separated off in a third column. A gas stream comprising monomethylamine and dimethylamine is taken off at the top of the third column and is passed to a fourth column. In the fourth column, the gas stream is separated into monomethylamine and dimethylamine. To separate off the methanol from the methanol-containing water from the third column, a further column can be installed downstream of the third column. The methanol obtained in the further column is, like the ammonia separated off in the first column, fed back into the methylamine synthesis.

Owing to the aggressive nature of the components in the product stream, the distillation columns which are preferably manufactured of carbon steel corrode. The addition of alkali metal hydroxide to the feed to the first column in alkylamine plants in order to prevent corrosion is known. However, when alkali metal hydroxide is added to the feed to the first column of the methylamine plant, blockages occur on the trays of the first column after only a short time.

It is an object of the present invention to provide a method of avoiding corrosion in the columns of the distillation plant in the preparation of methylamine.

We have found that this object is achieved by adding alkali metal hydroxide to the feed to the third column. When the alkali metal hydroxide is added to the feed to the third column, it is found that no corrosion occurs in the first and second column, although aggressive media are present in the gas stream there. Furthermore, the problem solution provided by the present invention avoids the formation of blockages in the first and second columns.

To isolate monomethylamine, dimethylamine and trimethylamine from the product gas stream obtained from the reaction of ammonia and methanol, the product gas stream is fed to a distillation plant. The product gas stream is fed into a first distillation column at a side inlet. In the first column, ammonia is separated off by pure distillation. The distillation is carried out at a pressure of preferably from 15 to 20 bar, in particular at a pressure of from 15 to 18 bar. The ammonia separated off as azeotrope with trimethylamine is taken off at the top of the first column and is preferably recirculated to the preparation of methylamine. The other constituents of the product gas stream form the bottoms and are taken off from the column and fed to a second column. The feed to the second column is likewise introduced at a side inlet. In the second column, trimethylamine is separated off by extractive distillation with addition of water. The trimethylamine is taken off at the top of the second column. The remaining components of the product gas stream which form the bottoms are fed into a third column at a side inlet. The water used for the extractive distillation in the second column and the water formed in the reaction and also unreacted methanol are taken off at the bottom of the third column. At the top of the third column, a mixture of monomethylamine and dimethylamine is taken off. The distillation in the third column is preferably carried out at a pressure of from 7 to 15 bar, in particular at a pressure of from 8 to 12 bar. The mixture of monomethylamine and dimethylamine taken off at the top of the third column is fed into a fourth column at a side inlet. In the fourth column, the stream comprising monomethylamine and dimethylamine is fractionally distilled at a pressure of preferably from 6 to 10 bar, in particular at a pressure of from 7 to 9 bar. Dimethylamine is obtained at the bottom of the fourth column and monomethylamine is taken off at the top of the fourth column.

To separate off the methanol from the water obtained in the distillation in the third column, it is possible to use a fifth column into which the methanol-containing water from a side offtake of the third column is fed. In the fifth column, the methanol is separated off by distillation. The methanol is taken off at the top of the fifth column and is recirculated to the reaction. The bottoms from the fifth column consist of water which has been freed of methanol and are recirculated to the third column.

In the problem solution provided by the present invention for avoiding corrosion in the distillation plant, alkali metal hydroxide is added to the feed to the third column. Alkali metal hydroxides which are suitable for the purposes of the invention are, in particular, sodium hydroxide and potassium hydroxide. The amount of alkali metal hydroxide has to be sufficient for unreacted alkali metal hydroxide to be present in the bottoms from the third column.

The columns are preferably heated by means of steam at a pressure of preferably from 10 to 20 bar and in particular a pressure in the range from 12 to 17 bar at the bottom of the columns.

The columns used for the distillation are preferably tray columns. Column trays of all construction types known to those skilled in the art are suitable. Apart from tray columns, it is also possible to use packed columns. Here, any packing geometry known to those skilled in the art can be used.

The product stream is preferably transported through the cascade of columns by means of the pressure difference between the individual columns.

The product gas stream comprises not only monomethylamine, dimethylamine and trimethylamine but also methanol and ammonia which have not reacted in the reaction and water formed as reaction by-product together with further by-products. Among these by-products, carbon monoxide, carbon dioxide, ammonium carbamate and formic acid in particular have a corrosive action toward iron. Addition of a base to neutralize the acids and to produce a basic environment can reduce or prevent corrosion of the iron.

As base to avoid corrosion, preference is given to adding alkali metal hydroxide, in particular sodium hydroxide or potassium hydroxide. The alkali metal hydroxide can be added in solid form or preferably as an aqueous solution.

When an aqueous alkali metal hydroxide solution is used, this preferably has a concentration of 25%.

It has surprisingly been found that when sodium hydroxide is added to the feed to the third column, no corrosion occurs in the distillation plant and no trays become blocked. Although the composition of the product stream in the second column differs from the composition in the third column only in that trimethylamine is present in the product stream in the second column and additional water is added in the third column, no corrosion occurs in the second column when the alkali metal hydroxide is added to the feed to the third column.

The amount of alkali metal hydroxide introduced has to be such that alkali metal hydroxide is still present in the bottoms from the third column.

Apart from the addition to the feed to the third column, the alkali metal hydroxide can also be added to the bottoms from the second column or be introduced directly into the stripping section of the second column.

BRIEF DESCRIPTION OF DRAWING

FIG. 1 shows a distillation plant configured according to the present invention for methylamine distillation.

DETAILED DESCRIPTION

A distillation plant configured according to the present invention for methylamine distillation comprises five columns as shown in FIG. 1. A product gas stream 10 obtained in the reaction of ammonia and methanol to form methylamines is fed into a first column 1 via a side inlet. In the first column 1, ammonia is separated off as an azeotrope with trimethylamine from the product stream by distillation. Ammonia 11 is taken off at the top of the first column 1 and is recirculated to the methylamine synthesis. The remaining components of the product stream 10 are obtained as bottoms 12 from the first column 1. The bottoms 12 from the first column 1 are fed into a second column 2 via a side inlet. In the second column 2, trimethylamine is separated off from the bottoms 12 from the first column 1 by extractive distillation. For the extractive distillation, water 13 is introduced into the second column 2 via a second side inlet. The second side inlet is located above the inlet for the bottoms 12 from the first column 1. Trimethylamine 14 is taken off at the top of the second column 2. The remaining components collect in the bottoms 15 from the second column 2. The bottoms 15 from the second column 2 are fed as feed 17 to a third column 3. Alkali 16 is added to the feed 17. Apart from the addition of the alkali 16 to the feed 17 to the third column 3, the alkali 16 can also be introduced into the bottoms 15 or into the stripping section of the second column 2. The alkali 16 is preferably an alkali metal hydroxide, in particular sodium hydroxide or potassium hydroxide in aqueous solution.

In the third column 3, monomethylamine and dimethylamine are separated off from the bottoms 15 from the second column 2 by distillation. The monomethylamine and dimethylamine are taken off as overhead stream 18 from the top of the third column 3 and fed to a fourth column 4. Water, methanol and further reaction by-products are present in the bottoms from the third column 3. To separate off the methanol from the bottoms from the third column 3, a fifth column 5 can be installed downstream of the third column 3. Methanol-containing water from the third column 3 is fed into the fifth column 5 via an inlet 20. In the fifth column 5, methanol is separated off from the water by distillation. The water which has been freed of methanol is recirculated via a return line 21 to the third column 3. The methanol 22 separated off is taken off at the top of the fifth column 5 and is recirculated to the methylamine synthesis. At the bottom of the third column 3, wastewater 19 which has been freed of methanol is taken off.

In the fourth column 4, the overhead stream 18 from the third column 3, which comprises, in particular, monomethylamine and dimethylamine, is separated into monomethylamine and dimethylamine. Monomethylamine 24 is taken off at the top of the fourth column 4. The dimethylamine 23 obtained as liquid phase in the fourth column 4 is taken off at the bottom of the fourth column 4.

EXAMPLE

A product stream obtained in the synthesis of methylamine is fractionated in a distillation plant. The columns are heated by means of steam at a pressure of 16 bar. In the first column, ammonia is separated off as an azeotrope with thrimethylamine from the product stream at a pressure of 16.5 bar. The remaining product stream is fed to a second column. In the second column, trimethylamine is separated off at a pressure of 14 bar and a temperature at the bottom of 160° C. and a temperature at the top of 103° C. and is taken off at the top of the second column. The bottoms from the second column are fed to a third column, with sodium hydroxide solution being added to the feed stream. In the third column, dimethylamine and monomethylamine are taken off at the top at a pressure of 8.3 bar and a temperature at the bottom of 178° C. and a temperature at the top of 68° C. The monomethylamine and dimethylamine are separated in a fourth column at a pressure of 7.5 bar and a temperature at the bottom of 74° C. and a temperature at the top of 53° C. Monomethylamine is taken off at the top of the fourth column and dimethylamine is taken off at the bottom of the fourth column. The methanol-containing water obtained via a side take-off in bottom of the third column is fed to a fifth column in vapour state which is operated at a pressure of 8.3 bar and a temperature at the bottom of 170° C. and a temperature at the top of 165° C. Methanol is taken off at the top of the fifth column. The water which has been freed of methanol is taken from the bottom of the fifth column and is fed back into the third column. The sodium hydroxide solution used has a concentration of 25% of NaOH. No corrosion in the columns is observed in the methylamine distillation carried out in this way.

LIST OF REFERENCE NUMERALS

1 First column
2 Second column
3 Third column
4 Fourth column
5 Fifth column
10 Product stream
11 Ammonia
12 Bottoms from the first column 1
13 Water
14 Trimethylamine
15 Bottoms from the second column 2
16 Alkali
17 Feed to the third column 3
18 Overhead stream from the third column 3
19 Wastewater
20 Feed to the fifth column 5
21 Recycle stream to the fifth column 5

22 Methanol
23 Dimethylamine
24 Monomethylamine

We claim:

1. A method of avoiding corrosion of a distillation plant for the separation of methylamines from a product stream which is obtained in the preparation of methylamines by gas-phase reaction of methanol and ammonia and which comprises monomethylamine, dimethylamine, trimethylamine, ammonia and methanol as components, wherein the separation comprises the steps of;

distilling the product stream in a first distillation column to separate off ammonia, feeding the remaining components of the product stream obtained as bottoms to a second column, carrying out an extractive distillation with introduction of water to separate off trimethylamine in the second column, feeding the further components of the product stream obtained as bottoms from the second column as feed to a third column, separating off monomethylamine and trimethylamine in the third column, and separating the monomethylamine and dimethylamine by distillation in a fourth column, wherein alkali metal hydroxide is added to the second or third column to prevent corrosion in the distillation plant.

2. A method as claimed in claim 1, wherein an additional fifth column is installed downstream of the third column, into the fifth column a stream taken from a side offtake or the bottom of the third column is fed and in the fifth column methanol is separated off by distillation.

3. A method as claimed in claim 2, wherein methanol-free water obtained as bottoms from the fifth column is recirculated to the third column.

4. A method as claimed in claim 1, wherein the alkali metal hydroxide is added to the feed to the third column.

5. A method as claimed in claim 1, wherein the alkali metal hydroxide is added to the bottom from the second column or is introduced into a stripping section of the second column.

6. A method as claimed in claim 1, wherein an amount of alkali metal hydroxide added is such that alkali metal hydroxide is still present in the bottoms from the third column.

7. A method as claimed in claim 1, wherein the alkali metal hydroxide is sodium hydroxide.

8. A method as claimed in claim 1, wherein the alkali metal hydroxide is potassium hydroxide.

* * * * *

UNITED STATES PATENT AND TRADEMARK OFFICE
CERTIFICATE OF CORRECTION

| | | |
|---|---|---|
| PATENT NO. | : 7,309,403 B2 | Page 1 of 1 |
| APPLICATION NO. | : 10/572783 | |
| DATED | : December 18, 2007 | |
| INVENTOR(S) | : Werner Reutemann et al. | |

It is certified that error appears in the above-identified patent and that said Letters Patent is hereby corrected as shown below:

On the Title Page:
In the ABSTRACT, please insert -- components -- between "The further" and "of".

In the Reference Cited,
On page 2 under FOREIGN PATENT DOCUMENTS, "JP 67-108041" should read -- JP 57-108041 --.

Signed and Sealed this

Twenty-fourth Day of June, 2008

JON W. DUDAS
*Director of the United States Patent and Trademark Office*